(12) United States Patent
Giri et al.

(10) Patent No.: US 10,568,531 B2
(45) Date of Patent: Feb. 25, 2020

(54) INTERLEAVED DUAL-CONTRAST UNENHANCED MAGNETIC RESONANCE ANGIOGRAPHY

(71) Applicants: Siemens Healthcare GmbH, Erlangen OT (DE); NorthShore University HealthSystem, Evanston, IL (US)

(72) Inventors: Shivraman Giri, Chicago, IL (US); Robert R. Edelman, Highland Park, IL (US)

(73) Assignees: Siemens Healthcare GmbH, Erlangen (DE); NorthShore University HealthSystem, Evanston, IL (US)

( * ) Notice: Subject to any disclaimer, the term of this patent is extended or adjusted under 35 U.S.C. 154(b) by 1048 days.

(21) Appl. No.: 14/927,655

(22) Filed: Oct. 30, 2015

(65) Prior Publication Data

US 2017/0119259 A1    May 4, 2017

(51) Int. Cl.
*A61B 5/026* (2006.01)
*G01R 33/563* (2006.01)
(Continued)

(52) U.S. Cl.
CPC ............ *A61B 5/0263* (2013.01); *A61B 5/055* (2013.01); *A61B 5/7425* (2013.01);
(Continued)

(58) Field of Classification Search
CPC ..... A61B 5/0263; A61B 5/055; A61B 5/7425; A61B 5/7475; A61B 2576/02; G01R 33/5635; G01R 33/4838
(Continued)

(56) References Cited

U.S. PATENT DOCUMENTS 8,332,010 B2    12/2012  Edelman
2003/0031351 A1*  2/2003  Yim ...................... G06K 9/342
                                                         382/130
(Continued)

OTHER PUBLICATIONS

Edelman, et al., "Quiescent-Interval Single Shot Unenhanced Magnetic Resonance Angiography of Peripheral Vascular Disease: Technical Considerations and Clinical Feasibility", Magn. Reson. Med. 63 (4): 951-958 (2010).

*Primary Examiner* — Amelie R Davis
*Assistant Examiner* — John Denny Li (57) ABSTRACT

A method for dual-contrast unenhanced magnetic resonance angiography includes iteratively acquiring flow-dependent slices and flow-independent slices in a region. Each iteration of the acquisition process comprises identifying a flow-dependent slice location within the region and identifying a flow-independent slice location upstream from the flow-dependent slice location according to blood flow in the region. Each iteration further includes applying a first radio frequency (RF) saturation pulse to the region such that MR signals from veins in the region are substantially suppressed, and applying a second RF saturation pulse to the flow-dependent slice location such that MR signals from background muscle and arterial blood in the region are substantially suppressed. A flow independent slice is acquired at the flow-independent slice location after the second RF saturation pulse is applied and before unsaturated arterial blood has maximally flowed into the region. After acquiring the flow-independent slice, a flow-dependent slice is acquired.

20 Claims, 6 Drawing Sheets

(51) Int. Cl.
*A61B 5/00* (2006.01)
*A61B 5/055* (2006.01)
*G01R 33/483* (2006.01)

(52) U.S. Cl.
CPC ........ *A61B 5/7475* (2013.01); *G01R 33/5635* (2013.01); *A61B 2576/02* (2013.01); *G01R 33/4838* (2013.01)

(58) Field of Classification Search
USPC ....................................................... 600/419
See application file for complete search history.

(56) References Cited

U.S. PATENT DOCUMENTS

| | | | | |
|---|---|---|---|---|
| 2005/0277828 | A1* | 12/2005 | Alsop | A61B 5/0263 600/419 |
| 2010/0160767 | A1* | 6/2010 | Deimling | G01R 33/5613 600/419 |
| 2013/0257429 | A1* | 10/2013 | Edelman | G01R 33/5635 324/309 |

* cited by examiner

INTERLEAVED DUAL-CONTRAST UNENHANCED MAGNETIC RESONANCE ANGIOGRAPHY

TECHNOLOGY FIELD

The present invention relates generally to methods, systems, and apparatuses for performing interleaved dual-contrast unenhanced magnetic resonance angiography. The disclosed technology may be applied, for example, to acquire multiple image sets of different contrasts without requiring extra time for enhancing the accuracy of angiography application.

BACKGROUND

Non-enhanced magnetic resonance angiography (NE-MRA) is a medical imaging technique used in the evaluation of vascular disease, especially in patients with impaired renal function. Most conventional NE-MRA techniques rely on flow properties of blood to generate sufficient contrast between blood-vessels and background for effective visualization of pathology. For example, during many clinical assessments, it is necessary to accentuate the arteries while suppressing the veins and all other tissues. The reliance on blood-flow presents challenges to contrast manipulation, considering that the flow patterns are different from subject to subject, and may be altered by vascular pathologies such as stenosis. Moreover, irregular heart rhythms can also affect flow, leading to sub-optimal contrast between arteries and other tissues.

An alternative approach that does not rely on blood-flow uses the natural contrast of blood and tissues to depict the pathology. However, the presence of background tissues and veins makes interpretation of images challenging for a clinician. Consequently, such an approach is not used traditionally in NE-MRA.

As a trade-off, in most conventional NE-MRA applications, blood-flow is used to manipulate contrast and extra time is built-in to permit sufficient inflow of blood, as well as to account for differences in blood-flow among subjects and differences between healthy vasculature and pathology. This extra time introduces inefficiency in the overall magnetic resonance (MR) acquisition process as the system remains idle which blood inflow occurs. Moreover, if the flow mechanism is compromised for any reason, the process must be repeated. Accordingly, it is desired to use the blood inflow time to acquire an additional set of images that has no reliance on blood flow (i.e., a flow-independent image set) that offers a back-up in the event that the flow mechanism is compromised for any reason.

SUMMARY

Embodiments of the present invention address and overcome one or more of the above shortcomings and drawbacks, by providing methods, systems, and apparatuses related to non-enhanced magnetic resonance angiography (NE-MRA) wherein flow-independent image data is acquired during delays inherent in the flow-dependent image acquisition process. Thus, the techniques described herein result in the acquisition of multiple image sets of different contrasts at no extra time for enhancing the accuracy of magnetic resonance angiography.

According to some embodiments, a method for acquiring non-contrast-enhanced magnetic resonance angiography with a magnetic resonance imaging (MRI) system includes performing an iterative acquisition process using the MRI system to acquire a plurality of flow-dependent slices and a plurality of flow-independent slices in a prescribed imaging region within a subject. Each iteration of the iterative acquisition process comprises identifying a flow-dependent slice location within the prescribed imaging region and identifying a flow-independent slice location upstream from the flow-dependent slice location according to blood flow in the prescribed imaging region. Additionally, in some embodiments a distance may be identified between the two slice locations. This distance will depend on blood flow velocity, which is different in different body regions. Each iteration of the iterative process further includes performing a pulse sequence such as for example, a balanced pulse sequence or a true fast imaging with steady state precession sequence (TrueFISP). This pulse sequence directs the MRI system to apply a first radio frequency (RF) saturation pulse to the prescribed imaging region such that MR signals from veins in the prescribed imaging region are substantially suppressed, and to apply a second RF saturation pulse to the flow-dependent slice location such that MR signals from background muscle and arterial blood in the prescribed imaging region are substantially suppressed. A flow independent slice is acquired at the flow-independent slice location during a time interval that begins at a first time point after which the second RF saturation pulse is applied and ends at a second time point at which unsaturated arterial blood has maximally flowed into the prescribed imaging region. After acquiring the flow independent slice, a flow-dependent slice is acquired at the flow-dependent slice location.

In some embodiments of the aforementioned method, the pulse sequence further directs the MRI system to apply a third RF saturation pulse to the prescribed imaging region such that MR signals from fat in the prescribed imaging region are substantially suppressed. In one embodiment, the aforementioned time interval ends prior to application of the third RF saturation pulse.

The aforementioned method may produce visual data that may be presented to users in a variety of ways. For example, in some embodiments, two images are generated: a flow-independent image of the prescribed imaging region based on the flow-independent slices and a flow-dependent image of the prescribed imaging region based on the flow-dependent slices. The flow-independent image and the flow-dependent image may then be presented in a stacked configuration in a graphical user interface In some embodiments of the aforementioned method, a signal indicative of a cardiac phase of the subject is acquired as part of the method. This signal may then be used, for example to determine the second time point at which the unsaturated arterial blood has maximally flowed into the prescribed imaging region.

According to other embodiments, an article of manufacture for acquiring non-contrast-enhanced magnetic resonance angiography with a magnetic resonance imaging (MRI) system comprises a non-transitory, tangible computer-readable medium holding computer-executable instructions for performing the aforementioned method, with or without the additional features discussed above.

According to other embodiments, a system for performing non-contrast-enhanced magnetic resonance angiography comprises a plurality of coils and a control computer. The control computer is configured to perform an iterative acquisition process to acquire a plurality of flow-dependent slices and a plurality of flow-independent slices in a prescribed imaging region within a subject. Each iteration of the iterative acquisition process performed by the control computer includes identifying a flow-dependent slice location within the prescribed imaging region and identifying a flow-independent slice location upstream from the flow-dependent slice location according to blood flow in the prescribed imaging region. Additionally, during each iteration, the control computer uses the plurality of coils to perform a pulse sequence comprising a first RF saturation pulse applied to the prescribed imaging region such that MR signals from veins in the prescribed imaging region are substantially suppressed, and a second RF saturation pulse applied to the flow-dependent slice location such that MR signals from background muscle and arterial blood in the prescribed imaging region are substantially suppressed. In some embodiments, the pulse sequence further comprises a third RF saturation pulse applied to the prescribed imaging region such that MR signals from fat in the prescribed imaging region are substantially suppressed. In these embodiments, the aforementioned time interval ends prior to application of the third RF saturation pulse.

The control computer uses the coils to acquire a flow independent slice at the flow-independent slice location during a time interval that begins at a first time point after which the second RF saturation pulse is applied and ends at a second time point at which unsaturated arterial blood has maximally flowed into the prescribed imaging region. After acquiring the flow-independent slice, the control computer uses the coils to acquire a flow-dependent slice at the flow-dependent slice location.

In some embodiments, the system further includes an electrocardiogram device configured to acquire a signal indicative of a cardiac phase of the subject. Then, during each iteration of the iterative acquisition process, the control computer may determine the second time point at which the unsaturated arterial blood has maximally flowed into the prescribed imaging region based on the acquired signal.

Additional features and advantages of the invention will be made apparent from the following detailed description of illustrative embodiments that proceeds with reference to the accompanying drawings.

BRIEF DESCRIPTION OF THE DRAWINGS

The foregoing and other aspects of the present invention are best understood from the following detailed description when read in connection with the accompanying drawings. For the purpose of illustrating the invention, there is shown in the drawings embodiments that are presently preferred, it being understood, however, that the invention is not limited to the specific instrumentalities disclosed. Included in the drawings are the following Figures.

DETAILED DESCRIPTION OF ILLUSTRATIVE EMBODIMENTS

The following disclosure describes the present invention according to several embodiments directed at methods, systems, and apparatuses related to dual-contrast non-enhanced magnetic resonance angiography (NE-MRA). The techniques described herein may be applied to efficiently acquire multiple image sets of different contrasts by interleaving acquisition of flow independent and flow dependent data.

Figure 1:
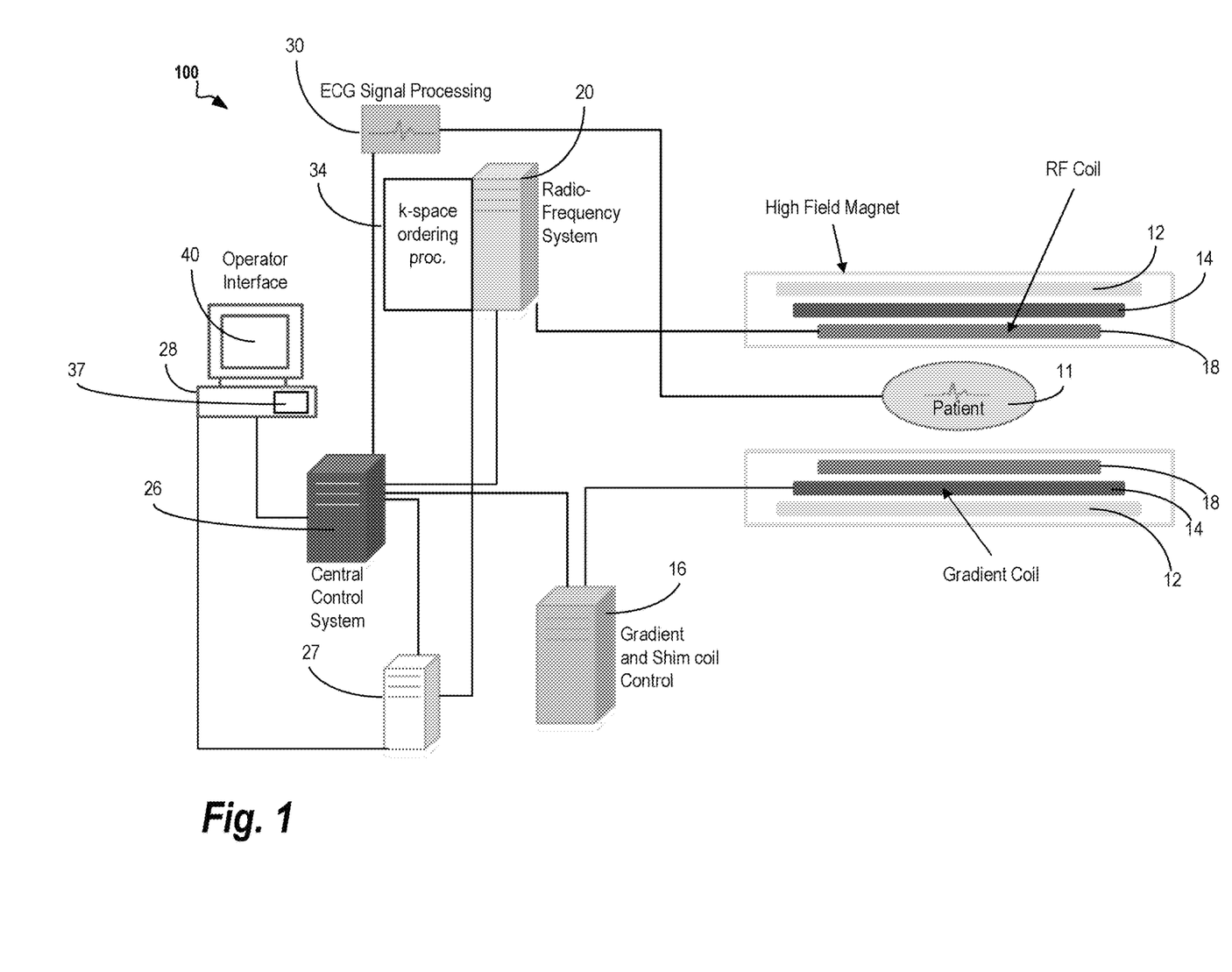
FIG. 1 shows a system for ordering acquisition of frequency domain components representing magnetic resonance image data for storage in a k-space storage array, as used by some embodiments of the present invention.

FIG. 1 shows a system 100 for ordering acquisition of frequency domain components representing MRI data for storage in a k-space storage array, as used by some embodiments of the present invention. In system 100, magnetic coils 12 create a static base magnetic field in the body of patient 11 to be imaged and positioned on a table. Within the magnet system are gradient coils 14 for producing position dependent magnetic field gradients superimposed on the static magnetic field. Gradient coils 14, in response to gradient signals supplied thereto by a gradient and shim coil control module 16, produce position dependent and shimmed magnetic field gradients in three orthogonal directions and generates magnetic field pulse sequences. The shimmed gradients compensate for inhomogeneity and variability in an MRI device magnetic field resulting from patient anatomical variation and other sources. The magnetic field gradients include a slice-selection gradient magnetic field, a phase-encoding gradient magnetic field and a readout gradient magnetic field that are applied to patient 11.

Further, radio frequency (RF) module 20 provides RF pulse signals to RF coil 18, which in response produces magnetic field pulses which rotate the spins of the protons in the imaged body of the patient 11 by ninety degrees or by one hundred and eighty degrees for so-called "spin echo" imaging, or by angles less than or equal to 90 degrees for so-called "gradient echo" imaging. Gradient and shim coil control module 16 in conjunction with RF module 20, as directed by central control unit 26, control slice-selection, phase-encoding, readout gradient magnetic fields, radio frequency transmission, and magnetic resonance signal detection, to acquire magnetic resonance signals representing planar slices of patient 11.

In response to applied RF pulse signals, the RF coil 18 receives magnetic resonance signals, i.e., signals from the excited protons within the body as they return to an equilibrium position established by the static and gradient magnetic fields. The magnetic resonance signals are detected and processed by a detector within RF module 20 and k-space component processor unit 34 to provide a magnetic resonance dataset to an image data processor for processing into an image. In some embodiments, the image data processor is located in central control unit 26. However, in other embodiments such as the one depicted in FIG. 1, the image data processor is located in a separate unit 27. ECG synchronization signal generator 30 provides ECG signals used for pulse sequence and imaging synchronization. A two or three dimensional k-space storage array of individual data elements in k-space component processor unit 34 stores corresponding individual frequency components comprising a magnetic resonance dataset. The k-space array of individual data elements has a designated center and individual data elements individually have a radius to the designated center.

A magnetic field generator (comprising coils 12, 14, and 18) generates a magnetic field for use in acquiring multiple individual frequency components corresponding to individual data elements in the storage array. The individual frequency components are successively acquired in an order in which the radius of respective corresponding individual data elements increases and decreases along a substantially spiral path as the multiple individual frequency components are sequentially acquired during acquisition of a magnetic resonance dataset representing an MR image. A storage processor in the k-space component processor unit 34 stores individual frequency components acquired using the magnetic field in corresponding individual data elements in the array. The radius of respective corresponding individual data elements alternately increases and decreases as multiple sequential individual frequency components are acquired. The magnetic field acquires individual frequency components in an order corresponding to a sequence of substantially adjacent individual data elements in the array and magnetic field gradient change between successively acquired frequency components are substantially minimized.

Central control unit 26 uses information stored in an internal database to process the detected magnetic resonance signals in a coordinated manner to generate high quality images of a selected slice(s) of the body (e.g., using the image data processor) and adjusts other parameters of system 100. The stored information comprises predetermined pulse sequence and magnetic field gradient and strength data as well as data indicating timing, orientation and spatial volume of gradient magnetic fields to be applied in imaging. Generated images are presented on display 40 of the operator interface. Computer 28 of the operator interface includes a graphical user interface (GUI) enabling user interaction with central control unit 26 and enables user modification of magnetic resonance imaging signals in substantially real time. Continuing with reference to FIG. 1, display processor 37 processes the magnetic resonance signals to reconstruct one or more images for presentation on display 40, for example. Various techniques may be used for reconstruction. For example, as described in greater detail below, an optimization algorithm is applied to iteratively solve a cost function which results in the reconstructed image.

As mentioned above, the conventional NE-MRA techniques rely on inflow of blood to generate the required contrast—accentuation of arteries and suppression of veins and background. These techniques typically have enough time intrinsically built in for adequate blood-flow. As a result, for a large proportion of time, the MR system is idle, i.e. no data is collected. For example, one example of a NE-MRA technique is quiescent interval shingle-shot (QISS). In this approach, the quiescent interval (QI) is a time during which no activity takes place so as to permit inflow of sufficient unsuppressed blood into the slice of interest. The MR signal acquired after the QI time represents only arterial signal. The process is then repeated for all slices, until the entire vascular anatomy of interest is covered. The series of slices are then stacked together to depict the vascular tree. While the QI time is necessary to enhance arterial conspicuity, it introduces a significant inefficiency in the throughput of MR data acquisition. Furthermore, the QI time may not suffice for adequate inflow of blood into certain arteries that are laterally oriented to the slice or in the presence of irregular heart rhythm.

Figure 2A:
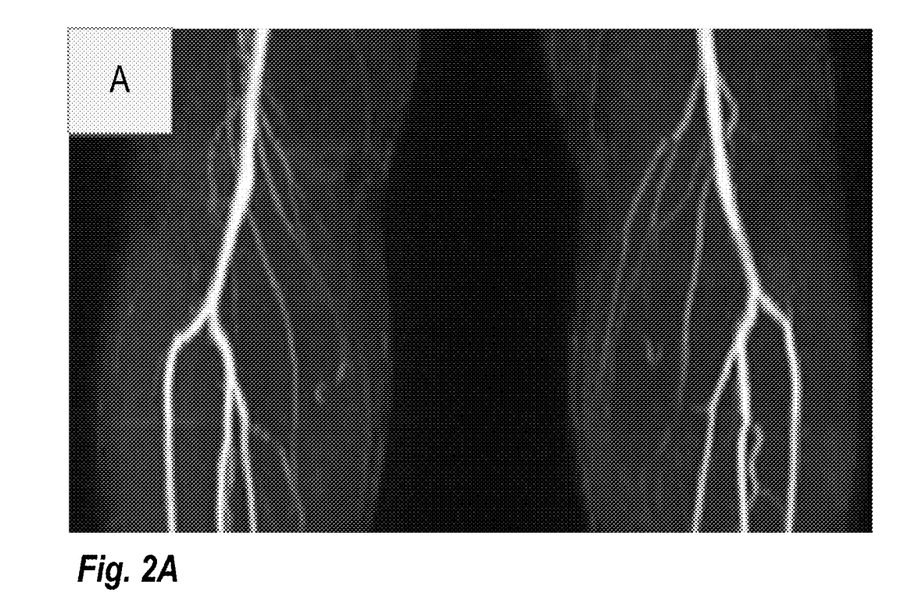
FIG. 2A provides an image of subject acquired using a conventional NE-MRA technique.
Figure 2B:
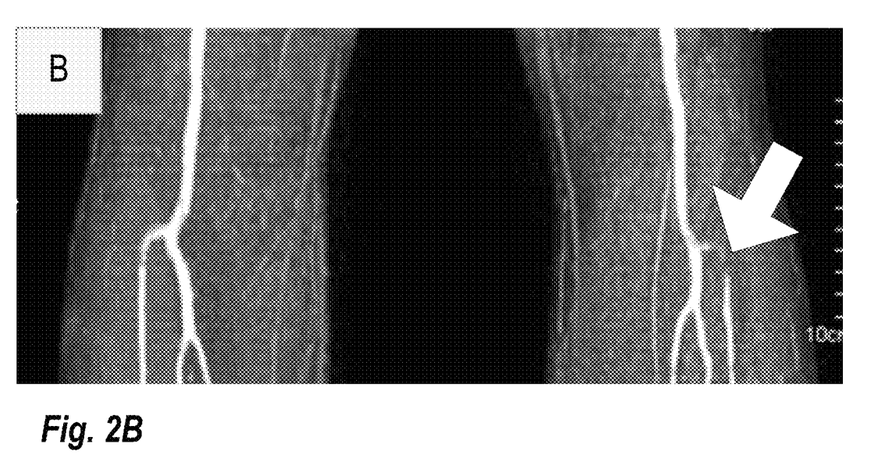
FIG. 2B provides an image showing the lateral orientation of some vessels leading to inadequate inflow of blood during the QI time into those vessels.
Figure 2C:
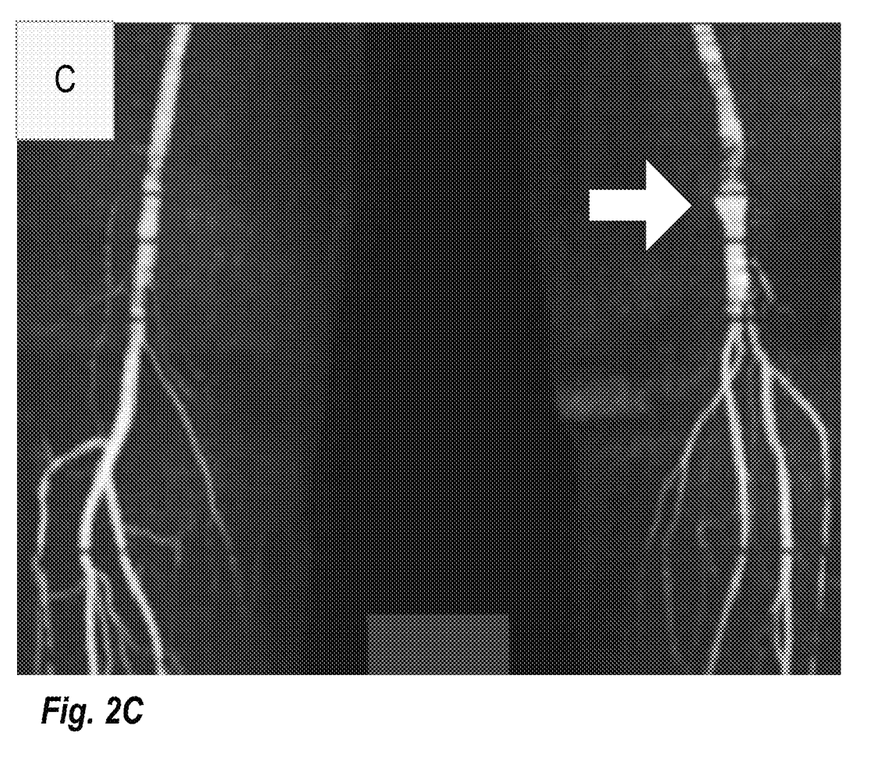
FIG. 2C shows a patient with irregular heart rhythm that resulted in non-uniform arterial flow in different slices.

FIGS. 2A-2C illustrate deficiencies in the conventional NE-MRA image acquisition process. More specifically, these figures provide examples of situations where the inflow of blood was sufficient for arterial conspicuity (FIG. 2A) and not sufficient (FIGS. 2B and 2C). In FIG. 2A, the subject had regular heart rhythm and vessels were oriented sufficiently perpendicular to the slice; as a result, the NE-MRA technique worked well. In FIG. 2B, the lateral orientation of some vessels (indicated by the arrow) led to inadequate inflow of blood during the QI time into those vessels. As a result, the artery is not clearly visible and mimics a pathology. FIG. 2C shows a patient with irregular heart rhythm that resulted in non-uniform arterial flow in different slices. The arterial signal is accordingly non-uniform across slices, leading to "striping" pattern that compromised depiction of pathology (as indicated by the arrow).

As shown in FIGS. 2A-C, there are situations where flow dependence leads to non-diagnostic images. This can be addressed by acquiring a set of images that does not rely on blood flow, and instead uses the native contrast of blood and tissue. This approach, however, has the drawback of not providing enough contrast between arteries and veins, and also between arteries and background tissues. As an alternative, one can acquire both sets of images, at the expense of doubling scan time. To address these problems, the techniques described herein use the QI time to acquire the other set of images that is unaffected by any suppression pulses, thus allowing reliance on native contrast.

Figure 3:
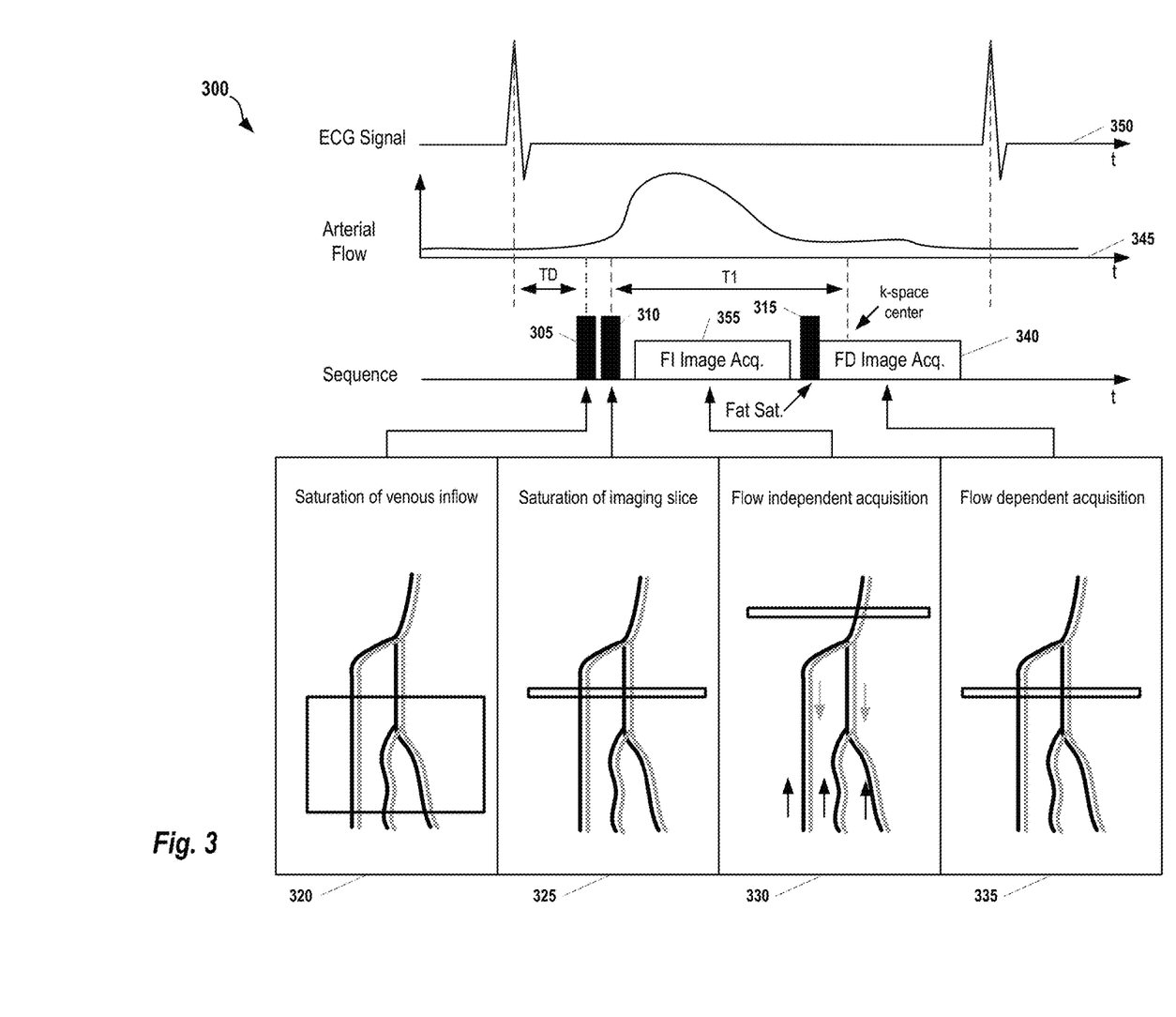
FIG. 3 illustrates a technique 300 to acquire flow-independent and flow-dependent magnetic resonance angiography during a single imaging session, according to some embodiments.

FIG. 3 illustrates a technique 300 to acquire flow-independent and flow-dependent magnetic resonance angiography during a single imaging session, according to some embodiments. This example shows how a slice of flow-independent and a slice of flow-dependent data can be acquired during application of a particular pulse sequence. An ECG Signal 350 is used to time application of the pulse sequence and image acquisition according to the subject's heartbeat and related arterial flow (as depicted in plot 345).

In FIG. 3, the pulse sequence includes three saturation pulses 305, 310, and 315. The first pulse 305 is used to suppress venous inflow suppression pulse in a region below the imaging plane as shown in box 320. The second pulse 310 is a spatial saturation pulse directed at the location of the imaging plane as depicted in box 325. Finally, third pulse 315 is a short-duration RF-pulse tuned to the resonance frequency of fat and applied immediately before the start of the flow dependent imaging sequence 340 in order to suppress the signal from fat in the imaging plane. Techniques for generating saturation pulses are generally known in the art and, thus, only briefly described herein.

Between the second pulse 310 and the third pulse 315, a flow independent imaging sequence 355 is performed to acquire a slice that is "upstream" (for arterial imaging) from the imaging plane. The flow independent imaging sequence 355 is illustrated in box 330. The length of the flow imaging sequence is equal (or approximately equal) to the QI time period discussed above. The location of the upstream slice is selected to minimize or eliminate any of the suppression resulting from the first pulse 305 and the second pulse 310. The distance between the upstream slice and the original slice in the imaging plane (saturated by the second pulse 310) may be selected based on factors such as the anatomical features of the area being imaged and/or the width of each slice. For example, different distances may be used depending on whether imaging is being performed on the subject's chest region versus leg or arm. The signal of the upstream slice is an aggregate from all possible tissues—arteries, veins, background tissue. Because this signal is independent of blood-flow, the contrast of the acquired image depends on the native characteristics of blood and tissues.

After acquiring the upstream slice and application of the third pulse 315 (i.e., the fat saturation pulse), the flow dependent imaging sequence 340 is applied to acquire the original slice corresponding to the signal that was saturated using the second pulse 310. This flow dependent imaging sequence 340 is illustrated in box 335. During acquisition of the upstream slice, there has been an inflow of blood into this original slice. Thus, the signal in the slice acquired using the flow dependent imaging sequence 340 will represent only that from arterial blood.

Various slice selection techniques may be applied. In general the order of slices is dependent upon factors such as the type of scanner, the slice acquisition technique, and number of slices being acquired. Using the techniques described herein, the region being imaged may be divided into an upstream section and a downstream section. Within each section, slices may be acquired in a manner that allows the acquisition technique and the number of slices to be varied, if desired. Alternatively, the region may be imaged without any division by designating an artificial boundary within the imaged region dividing the upstream and downstream sections. The slice acquisition technique can then be configured to ensure that all upstream slices are acquired above the boundary and all other slices are acquired below the boundary.

Figure 4:
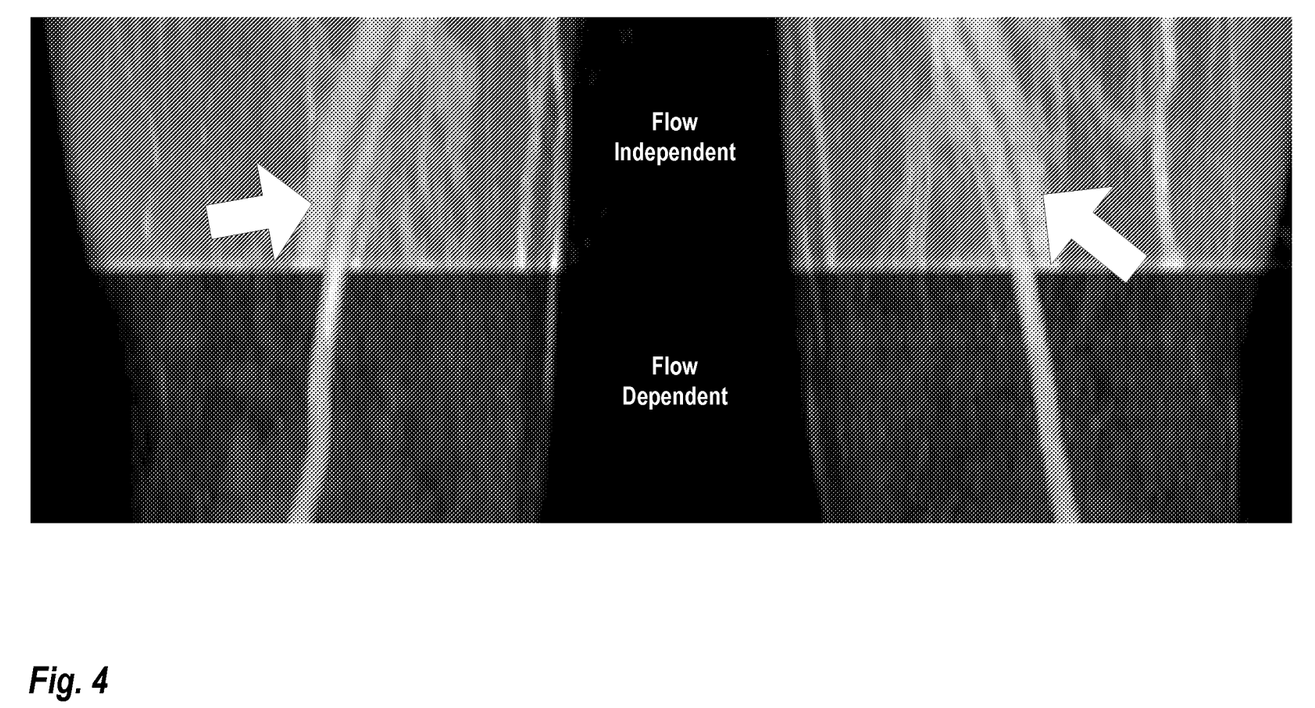
FIG. 4 provides two sets of images acquired using the technique illustrated in FIG. 3.

FIG. 4 provides two sets of images acquired using the technique illustrated in FIG. 3. The images have been stacked together to better depict the underlying contrast, the upper half showing the flow-independent stack, whereas the lower half showing the flow-dependent. The upper half represents native contrast of blood and background tissue. As a result, one cannot distinguish between veins (indicated by the arrows) and arteries. Moreover, the background is not suppressed, compromising the contrast between background and blood vessels. The lower half shows flow-dependent case whereby veins are suppressed and only arteries are visible. Furthermore, the background is nicely suppressed, enhancing the visibility of arteries.

In a clinical setting, one would normally use the flow-dependent image set for image analysis. The additional image from the flow-independent acquisition can be referenced to resolve uncertainty in cases where flow-dependent image(s) performed sub-optimally, such as those shown in FIGS. 2B and 2C. Alternatively, in some embodiments, the flow-independent image may be presented in graphical user interface using a stacked configuration as presented in FIG. 4. This allows the clinician to directly analyze the imaged region simultaneously with the different types of contrast. In addition to (or as an alternative to) direct presentation, in some embodiments the flow independent image may be used to create a subtraction mask which may then be applied to the flow dependent image to further refine visualization of anatomical features in the imaged region.

Figure 5:
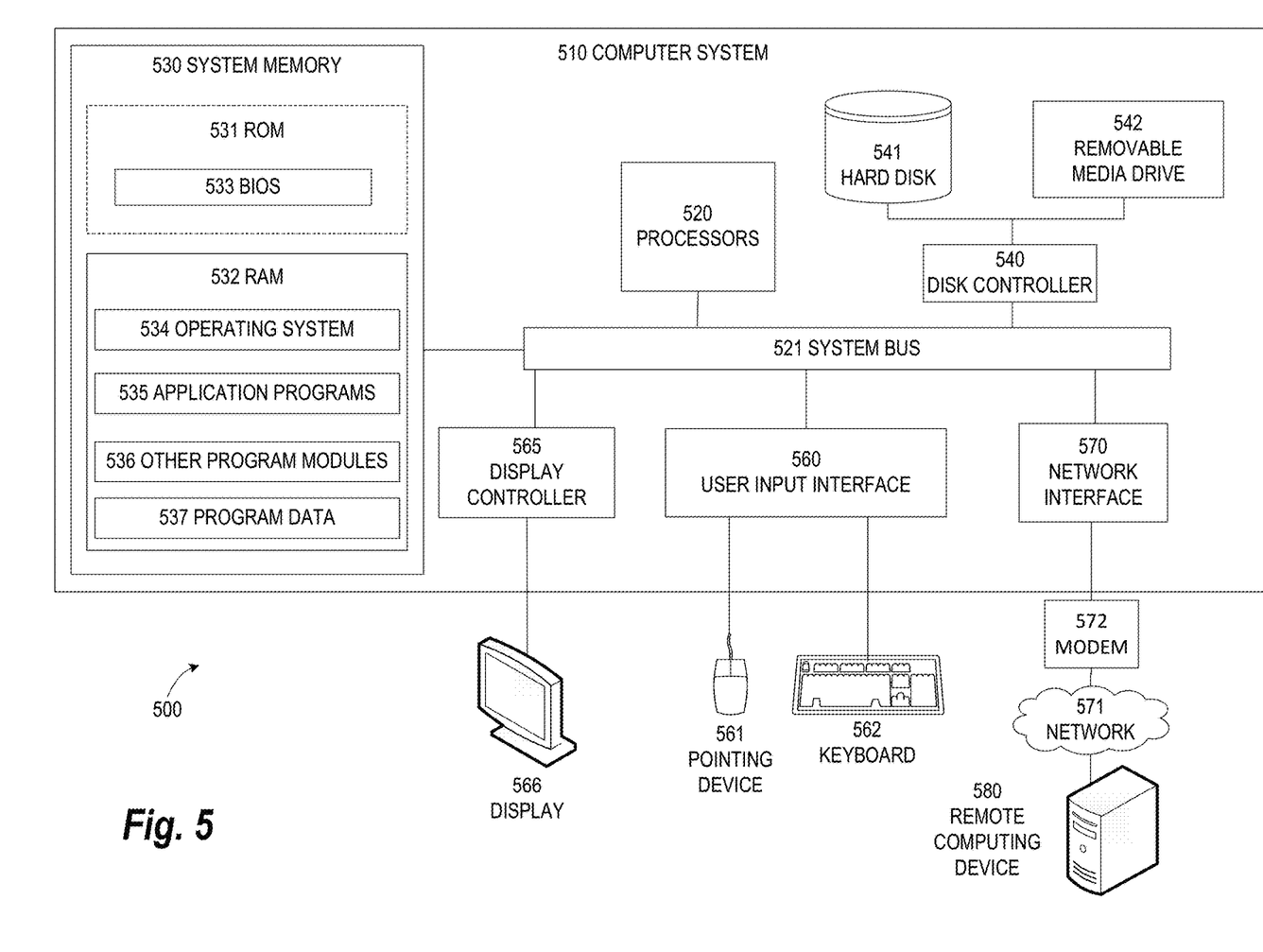
FIG. 5 illustrates an exemplary computing environment within which embodiments of the invention may be implemented.

FIG. 5 illustrates an exemplary computing environment 500 within which embodiments of the invention may be implemented. For example, this computing environment 500 may be used to implement the technique 300 described above with respect to FIG. 3. In some embodiments, the computing environment 500 may be used to implement one or more of the components illustrated in the system 100 of FIG. 1. The computing environment 500 may include computer system 510, which is one example of a computing system upon which embodiments of the invention may be implemented. Computers and computing environments, such as computer system 510 and computing environment 500, are known to those of skill in the art and thus are described briefly here.

As shown in FIG. 5, the computer system 510 may include a communication mechanism such as a bus 521 or other communication mechanism for communicating information within the computer system 510. The computer system 510 further includes one or more processors 520 coupled with the bus 521 for processing the information. The processors 520 may include one or more central processing units (CPUs), graphical processing units (GPUs), or any other processor known in the art.

The computer system 510 also includes a system memory 530 coupled to the bus 521 for storing information and instructions to be executed by processors 520. The system memory 530 may include computer readable storage media in the form of volatile and/or nonvolatile memory, such as read only memory (ROM) 531 and/or random access memory (RAM) 532. The system memory RAM 532 may include other dynamic storage device(s) (e.g., dynamic RAM, static RAM, and synchronous DRAM). The system memory ROM 531 may include other static storage device(s) (e.g., programmable ROM, erasable PROM, and electrically erasable PROM). In addition, the system memory 530 may be used for storing temporary variables or other intermediate information during the execution of instructions by the processors 520. A basic input/output system (BIOS) 533 containing the basic routines that help to transfer information between elements within computer system 510, such as during start-up, may be stored in ROM 531. RAM 532 may contain data and/or program modules that are immediately accessible to and/or presently being operated on by the processors 520. System memory 530 may additionally include, for example, operating system 534, application programs 535, other program modules 536 and program data 537.

The computer system 510 also includes a disk controller 540 coupled to the bus 521 to control one or more storage devices for storing information and instructions, such as a hard disk 541 and a removable media drive 542 (e.g., floppy disk drive, compact disc drive, tape drive, and/or solid state drive). The storage devices may be added to the computer system 510 using an appropriate device interface (e.g., a small computer system interface (SCSI), integrated device electronics (IDE), Universal Serial Bus (USB), or FireWire).

The computer system 510 may also include a display controller 565 coupled to the bus 521 to control a display 566, such as a cathode ray tube (CRT) or liquid crystal display (LCD), for displaying information to a computer user. The computer system includes an input interface 560 and one or more input devices, such as a keyboard 562 and a pointing device 561, for interacting with a computer user and providing information to the processor 520. The pointing device 561, for example, may be a mouse, a trackball, or a pointing stick for communicating direction information and command selections to the processors 520 and for controlling cursor movement on the display 566. The display 566 may provide a touch screen interface which allows input to supplement or replace the communication of direction information and command selections by the pointing device 561.

The computer system 510 may perform a portion or all of the processing steps of embodiments of the invention in response to the processors 520 executing one or more sequences of one or more instructions contained in a memory, such as the system memory 530. Such instructions may be read into the system memory 530 from another computer readable medium, such as a hard disk 541 or a removable media drive 542. The hard disk 541 may contain one or more datastores and data files used by embodiments of the present invention. Datastore contents and data files may be encrypted to improve security. The processors 520 may also be employed in a multi-processing arrangement to execute the one or more sequences of instructions contained in system memory 530. In alternative embodiments, hard-wired circuitry may be used in place of or in combination with software instructions. Thus, embodiments are not limited to any specific combination of hardware circuitry and software.

As stated above, the computer system 510 may include at least one computer readable medium or memory for holding instructions programmed according to embodiments of the invention and for containing data structures, tables, records, or other data described herein. The term "computer readable medium" as used herein refers to any medium that participates in providing instructions to the processor 520 for execution. A computer readable medium may take many forms including, but not limited to, non-volatile media, volatile media, and transmission media. Non-limiting examples of non-volatile media include optical disks, solid state drives, magnetic disks, and magneto-optical disks, such as hard disk 541 or removable media drive 542. Non-limiting examples of volatile media include dynamic memory, such as system memory 530. Non-limiting examples of transmission media include coaxial cables, copper wire, and fiber optics, including the wires that make up the bus 521. Transmission media may also take the form of acoustic or light waves, such as those generated during radio wave and infrared data communications.

The computing environment 500 may further include the computer system 510 operating in a networked environment using logical connections to one or more remote computers, such as remote computer 580. Remote computer 580 may be a personal computer (laptop or desktop), a mobile device, a server, a router, a network PC, a peer device or other common network node, and typically includes many or all of the elements described above relative to computer system 510. When used in a networking environment, computer system 510 may include modem 572 for establishing communications over a network 571, such as the Internet. Modem 572 may be connected to bus 521 via user network interface 570, or via another appropriate mechanism.

Network 571 may be any network or system generally known in the art, including the Internet, an intranet, a local area network (LAN), a wide area network (WAN), a metropolitan area network (MAN), a direct connection or series of connections, a cellular telephone network, or any other network or medium capable of facilitating communication between computer system 510 and other computers (e.g., remote computer 580). The network 571 may be wired, wireless or a combination thereof. Wired connections may be implemented using Ethernet, Universal Serial Bus (USB), RJ-11 or any other wired connection generally known in the art. Wireless connections may be implemented using Wi-Fi, WiMAX, and Bluetooth, infrared, cellular networks, satellite or any other wireless connection methodology generally known in the art. Additionally, several networks may work alone or in communication with each other to facilitate communication in the network 571.

The embodiments of the present disclosure may be implemented with any combination of hardware and software. In addition, the embodiments of the present disclosure may be included in an article of manufacture (e.g., one or more computer program products) having, for example, computer-readable, non-transitory media. The media has embodied therein, for instance, computer readable program code for providing and facilitating the mechanisms of the embodiments of the present disclosure. The article of manufacture can be included as part of a computer system or sold separately.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters.

A graphical user interface (GUI), as used herein, comprises one or more display images, generated by a display processor and enabling user interaction with a processor or other device and associated data acquisition and processing functions. The GUI also includes an executable procedure or executable application. The executable procedure or executable application conditions the display processor to generate signals representing the GUI display images. These signals are supplied to a display device which displays the image for viewing by the user. The processor, under control of an executable procedure or executable application, manipulates the GUI display images in response to signals received from the input devices. In this way, the user may interact with the display image using the input devices, enabling user interaction with the processor or other device.

The functions and process steps herein may be performed automatically or wholly or partially in response to user command. An activity (including a step) performed automatically is performed in response to one or more executable instructions or device operation without user direct initiation of the activity.

The system and processes of the figures are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. As described herein, the various systems, subsystems, agents, managers and processes can be implemented using hardware components, software components, and/or combinations thereof. No claim element herein is to be construed under the provisions of 35 U.S.C. 112, sixth paragraph, unless the element is expressly recited using the phrase "means for."

We claim:

1. A method for acquiring non-contrast-enhanced magnetic resonance angiography with a magnetic resonance imaging (MRI) system, the method comprising:

performing an iterative acquisition process using the MRI system to acquire a plurality of flow-dependent slices and a plurality of flow-independent slices in a prescribed imaging region within a subject, wherein each iteration of the iterative acquisition process comprises:
identifying a flow-dependent slice location within the prescribed imaging region;
identifying a flow-independent slice location upstream from the flow-dependent slice location according to blood flow in the prescribed imaging region; and
performing a pulse sequence that directs the MRI system to:
apply a first radio frequency (RF) saturation pulse to the prescribed imaging region to substantially suppress MR signals from veins in the prescribed imaging region, and
apply a second RF saturation pulse to the flow-dependent slice location to substantially suppress MR signals from background muscle and arterial blood in the prescribed imaging region;
acquire a flow-independent slice at the flow-independent slice location during a time interval that begins at a first time point after which the second RF saturation pulse is applied and ends before a second time point at which unsaturated arterial blood has maximally flowed into the prescribed imaging region; and
after acquiring the flow-independent slice, acquire a flow-dependent slice at the flow-dependent slice location.

2. The method of claim 1, wherein the pulse sequence further directs the MRI system to:
apply a third RF saturation pulse to the prescribed imaging region such that MR signals from fat in the prescribed imaging region are substantially suppressed.

3. The method of claim 2, wherein the time interval ends prior to application of the third RF saturation pulse.

4. The method of claim 1, further comprising:
generating a flow-independent image of the prescribed imaging region using the plurality of flow-independent slices;
generating a flow-dependent image of the prescribed imaging region using the plurality of flow-dependent slices.

5. The method of claim 4, further comprising:
presenting the flow-independent image and the flow-dependent image in a stacked configuration in a graphical user interface.

6. The method of claim 1, further comprising:
acquiring a signal indicative of a cardiac phase of the subject.

7. The method of claim 6, further comprising:
determining the second time point at which the unsaturated arterial blood has maximally flowed into the prescribed imaging region based on the signal indicative of the cardiac phase of the subject.

8. The method of claim 1, wherein the pulse sequence is a balanced pulse sequence.

9. The method of claim 1, wherein the pulse sequence is a true fast imaging with steady state precession sequence.

10. An article of manufacture for acquiring non-contrast-enhanced magnetic resonance angiography with a magnetic resonance imaging (MRI) system, the article of manufacture comprising a non-transitory, tangible computer-readable medium holding computer-executable instructions for performing a method comprising:
performing an iterative acquisition process using the MRI system to acquire a plurality of flow-dependent slices and a plurality of flow-independent slices in a prescribed imaging region within a subject, wherein each iteration of the iterative acquisition process comprises:
identifying a flow-dependent slice location within the prescribed imaging region;
identifying a flow-independent slice location upstream from the flow-dependent slice location according to blood flow in the prescribed imaging region;
directing the MRI system to perform a pulse sequence comprising:
applying a first radio frequency (RF) saturation pulse to the prescribed imaging region such that MR signals from veins in the prescribed imaging region are substantially suppressed,
applying a second RF saturation pulse to the flow-dependent slice location such that MR signals from background muscle and arterial blood in the prescribed imaging region are substantially suppressed;
acquiring a flow-independent slice at the flow-independent slice location during a time interval that begins at a first time point after which the second RF saturation pulse is applied and ends before a second time point at which unsaturated arterial blood has maximally flowed into the prescribed imaging region; and
acquiring a flow-dependent slice at the flow-dependent slice location after acquiring the flow-independent slice.

11. The article of manufacture of claim 10, wherein the pulse sequence further comprises:
applying a third RF saturation pulse to the prescribed imaging region such that MR signals from fat in the prescribed imaging region are substantially suppressed.

12. The article of manufacture of claim 11, wherein the time interval ends prior to application of the third RF saturation pulse.

13. The article of manufacture of claim 10, wherein the method further comprises
generating a flow-independent image of the prescribed imaging region using the plurality of flow-independent slices;
generating a flow-dependent image of the prescribed imaging region using the plurality of flow-dependent slices.

14. The article of manufacture of claim 13, wherein the method further comprises:
presenting the flow-independent image and the flow-dependent image in a stacked configuration in a graphical user interface.

15. The article of manufacture of claim 10, wherein the method further comprises:
acquiring a signal indicative of a cardiac phase of the subject.

16. The article of manufacture of claim 15, wherein the method further comprises:
determining the second time point at which the unsaturated arterial blood has maximally flowed into the prescribed imaging region based on the signal indicative of the cardiac phase of the subject.

17. The article of manufacture of claim 10, wherein the pulse sequence is a balanced pulse sequence.

18. A system for performing non-contrast-enhanced magnetic resonance angiography, the system comprising:
a plurality of coils;
a control computer configured to perform an iterative acquisition process to acquire a plurality of flow-dependent slices and a plurality of flow-independent slices in a prescribed imaging region within a subject, wherein each iteration of the iterative acquisition process comprises:

identifying a flow-dependent slice location within the prescribed imaging region;

identifying a flow-independent slice location upstream from the flow-dependent slice location according to blood flow in the prescribed imaging region;

using the plurality of coils to perform a pulse sequence comprising:
- a first radio frequency (RF) saturation pulse applied to the prescribed imaging region such that MR signals from veins in the prescribed imaging region are substantially suppressed;
- a second RF saturation pulse applied to the flow-dependent slice location such that MR signals from background muscle and arterial blood in the prescribed imaging region are substantially suppressed;
- a first acquisition pulse to acquire a flow-independent slice at the flow-independent slice location during a time interval that begins at a first time point after which the second RF saturation pulse is applied and ends before a second time point at which unsaturated arterial blood has maximally flowed into the prescribed imaging region; and
- a second acquisition pulse to acquire a flow-dependent slice at the flow-dependent slice location after acquiring the flow-independent slice.

19. The system of claim 18, wherein the pulse sequence further comprises:
a third RF saturation pulse applied to the prescribed imaging region such that MR signals from fat in the prescribed imaging region are substantially suppressed,
wherein the time interval ends prior to application of the third RF saturation pulse.

20. The system of claim 18, further comprising:
an electrocardiogram device configured to acquire a signal indicative of a cardiac phase of the subject,
wherein, during each iteration of the iterative acquisition process, the control computer is configured to determine the second time point at which the unsaturated arterial blood has maximally flowed into the prescribed imaging region based on the signal indicative of the cardiac phase of the subject.

* * * * *